(12) United States Patent
Storm

(10) Patent No.: US 6,571,124 B1
(45) Date of Patent: May 27, 2003

(54) APPARATUS AND METHOD FOR MONITORING SKIN CONDUCTANCE AND METHOD FOR CONTROLLING A WARNING SIGNAL

(76) Inventor: Hanne Storm, Gimle Terrasse 4, N-0264 Oslo (NO)

( * ) Notice: Subject to any disclaimer, the term of this patent is extended or adjusted under 35 U.S.C. 154(b) by 0 days.

(21) Appl. No.: 09/980,191

(22) PCT Filed: May 31, 2000

(86) PCT No.: PCT/NO00/00186
§ 371 (c)(1),
(2), (4) Date: Nov. 30, 2001

(87) PCT Pub. No.: WO00/72751
PCT Pub. Date: Dec. 7, 2000

(30) Foreign Application Priority Data

Jun. 1, 1999 (NO) ................................................ 992635

(51) Int. Cl.$^7$ ................................................ A61B 5/00
(52) U.S. Cl. ................. 600/547; 600/300; 600/306; 600/557
(58) Field of Search ................. 600/306, 547, 600/557, 300

(56) References Cited

U.S. PATENT DOCUMENTS

| | | | |
|---|---|---|---|
| 4,291,708 A | | 9/1981 | Frei et al. |
| 4,697,599 A | | 10/1987 | Woodley et al. |
| 4,844,091 A | * | 7/1989 | Bellak .................. 600/547 |
| 5,897,505 A | | 4/1999 | Feinberg et al. |
| 6,146,334 A | * | 11/2000 | Laserow .................. 600/552 |
| 6,347,238 B1 | * | 2/2002 | Levengood et al. ........ 600/547 |

FOREIGN PATENT DOCUMENTS

| | | |
|---|---|---|
| FR | 2 485 364 | 12/1981 |
| GB | 2 291 971 | 2/1996 |
| JP | 9-19420 | 1/1997 |
| JP | 10-99288 | 4/1998 |
| WO | WO85/00785 | 2/1985 |
| WO | WO86/01317 | 2/1986 |

OTHER PUBLICATIONS

Venables, P.H., "Autonomic activity," *Annals of the NY Academy of Sciences*, 620:191–207 (1991).
Lidberg et al., "Sympathetic skin nerve discharges in relation to amplitude of skin resistance responses," *Psychophysiology*, 18:3:268–270 (1981).
Edelberg R., "Electrical properties of the skin," *Methods in Psychophysiology*, 1–53.
Fremming, A.D., "IEC 60601 compatible PC–based data logger system" Post–graduate thesis, Institute of Physics, University of Oslo (1998).
Grimnes et al., *Bioimpedance and Bioelectricity Basics*, Academic Press, 296–299 (2000).
Grimnes, S., "Impedance measurement of individual skin surface electrodes," *Medical & Biological Engineering & Computing*, 21:750–755 (1983).
Martin et al., *Techniques in Psychophysiology*, John Wiley & Sons, "Electrodermal activity," (1980).
Martinsen O.G., "Development of a portable instrument for measuring skin admittance," Post–graduate thesis, Institute of Physics, University of Oslo (1990).
Odegarden S.R., "Logging and analyzing of medical data— special parameters for electrodermal activity," Post–graduate thesis, Institute of Physics, University of Oslo (1998).

* cited by examiner

*Primary Examiner*—Robert L. Nasser
(74) *Attorney, Agent, or Firm*—Merchant & Gould, P.C.

(57) ABSTRACT

The invention relates to an apparatus and a method for monitoring the autonomous nervous system in an individual, especially for detecting pain, by utilizing spontaneous change in skin conductance. The apparatus comprises measuring equipment (3, 4) for measuring the skin's conductance, and storage and processing means (5) for deriving secondary characteristics of the conductance signal, thus enabling it by means of signal means (6) to indicate that the pain or other activity in the autonomous nervous system has reached a certain threshold. The invention also relates to a method for controlling a warning signal (7) in such an apparatus.

21 Claims, 2 Drawing Sheets

Figure 1:
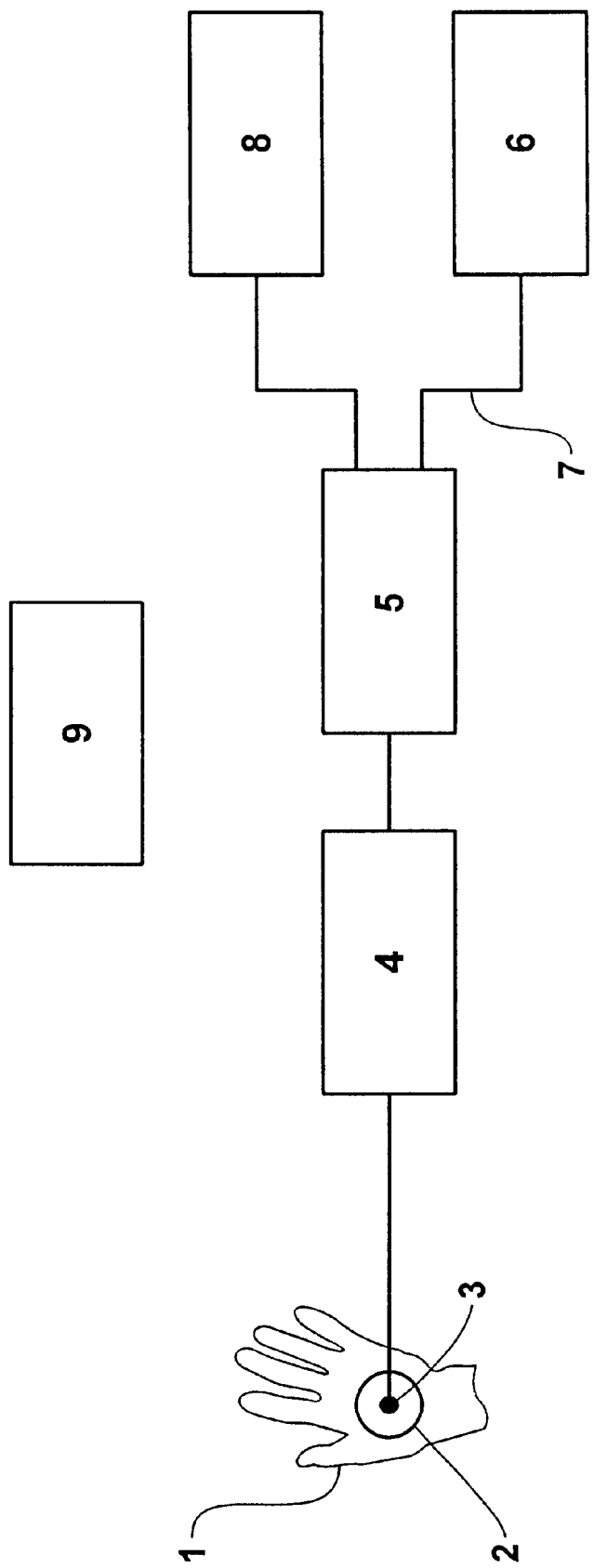

APPARATUS AND METHOD FOR MONITORING SKIN CONDUCTANCE AND METHOD FOR CONTROLLING A WARNING SIGNAL

The invention relates to an apparatus and a method for monitoring the autonomous nervous system of an individual, especially for detecting pain.

The invention also relates to a method for controlling a warning signal in an apparatus for monitoring the autonomous nervous system of an individual, especially for detecting pain.

In the field of medical technology there is a problem in producing physical measurements representing the activity in an individual's autonomous nervous system, i.e. in the part of the nervous system which is beyond the control of the will. It is particularly important to obtain indications of the activity in the sympathetic nervous system. For example, in various situations there is a need to monitor a patient's experience of pain.

There is a special need to monitor the sympathetic nervous system in babies. It is known that babies with apnea (a cessation of breathing for more than 20 seconds) and attacks of lifelessness exhibit changes in the degree of activity in the sympathetic nervous system. The indications are, therefore, that monitoring the sympathetic nervous system of babies may contribute towards revealing dysfunctions in the nervous system, and that such monitoring can also be used to warn of the risk of cot death.

A method and an apparatus for monitoring the autonomous nervous system in an individual will also be applicable in other situations. In the case of both premature babies, infants and other individuals, both children and adults, there may be a need to observe pain reactions. This applies in particular to cases where the individual himself is unable to express the experience of pain in the normal manner, for example verbally, by means of crying or facial expression.

An example of this kind of application is monitoring of premature babies. These babies have a special need for pain monitoring, since they have poorly developed facial expression, in addition to which they may lack the energy to cry. In premature babies pain or stress have been associated with the occurrence of cerebral haemorrhage, and it has also been shown that their experience of pain can be remembered, thereby affecting their future pain reactions. It is therefore vital to know in real time when such babies are exposed to pain, in order, amongst other things, to be able to administer analgesics.

Another application is monitoring of patients in a respirator.

The sympathetic nervous system can be activated by the feeling of pain, but also by other factors such as stress, fear and anger. When the sympathetic nervous system is activated, it causes reactions such as increased heart rate, increased blood pressure and increased emotional perspiration. Blood pressure, pulse and respiration rate are controlled both by the sympathetic and parasympathetic nervous system, as well as being affected by other factors, such as if the patient loses a lot of blood, or has lung or heart disease. Of all these phenomena, therefore, increased emotional perspiration is the most specific target for the activity, particularly for detecting pain response in the sympathetic nervous system.

A known phenomenon associated with emotional perspiration is that the skin's conductance, particularly on specific parts of the body such as in the palms of the hands and the soles of the feet, is influenced by the activity in the sympathetic nervous system, caused among other things by stimulation of the sense of pain. On exposure to pain stimuli or other stress the sympathetic activity in efferent nerve fibres to the sweat glands increases. When the sympathetic nerves are activated, the sweat glands are activated, the sweat channels are filled with liquid, and the conductance in the skin increases. When the liquid evaporates, the skin conductance decreases. In this manner fluctuations arise in the skin conductance. This phenomenon is called spontaneous skin conductance. The spontaneous skin conductance consists of waves and a basal level. The number of waves and the height of the waves indicate direct sympathetic activity in the nerves.

The basal level, however, does not constitute a satisfactory basis for drawing conclusions concerning the activity of the patients sympathetic nervous system, including the presumed pain condition. Amongst other things this is due to the fact that after a pain or other nervous system stimulation, the total skin moisture level and thereby the conductance signal takes a relatively long time to return to its basal level (the so-called recovery time).

However, tests have shown that the skin's conductance appears as a time variable signal which, in addition to a basal, slowly varying value (the so-called basal level), also has a component consisting of spontaneous waves or fluctuations, in which characteristics of these fluctuations, such as for example their frequency and amplitude, are factors which are correlated with the experience of pain in the target object (the patient). Measuring and analysing characteristics of these fluctuations may therefore be a suitable method of providing fast and reliable information concerning the activity in the sympathetic nervous system, including the effect of pain.

Tests which compare the activity in the sympathetic nervous system with skin conductance, where the frequency of maximum values and the fluctuations in the skin's conductance are taken into account, are known from, amongst others, Edelberg R: *Electrical Properties of the Skin.* Methods in psychophysiology (Brown, C. C. (ed.)), Ch. 1, The Williams & Wilkins Company 1967, pp. 1–50, and from Lidberg L., Wallin G. *Sympathetic skin nerve discharges in relation to amplitude of skin resistance responses.* Psychophysiology 1981;18(3):268–270.

Previously known systems for analysing skin conductance comprise a data acquisition system for recording a series of measurements for the skin's conductance, and a computer for subsequent analysis of the recorded series of measurements. The analysis therefore takes place after the data have been collected, and thereby after the autonomous nervous activity in the patient, as well as the sensations which gave rise to the nervous activity, have already ceased. Such systems therefore offer no possibility of real time monitoring of the patient's autonomous nervous activity and pain reaction. In particular, they offer no possibility of detecting and warning that a limit for pain reaction has been exceeded during the period in which the measurements are performed.

From the patent literature several solutions are known which have some points of resemblance with the present invention:

U.S. Pat. No. 5,897,505 discloses a diagnostic apparatus for assessing pain in a human being, based on skin conductance and temperature measurement. The apparatus is intended for performing a single measurement at a time, and to indicate the result of this measurement on a display. The apparatus also includes auto-scaling and overrange functions which implies that two subsequent measurements are performed, in order to determine the appropriate scaling of the input signal and possibly to indicate an overrange warning signal. The apparatus does not permit the continuous monitoring and analysis of spontaneous response in skin conductance, particularly not the amplitude and frequency of fluctuations in the skin conductance signal, caused by pain or similar activities in the autonomous nervous system of the individual.

WO 85/00785 discloses an attention monitor based on skin resistance measurement. A warning signal is activated when the measured resistance exceeds a predetermined amount. The publication does not indicate or suggest the analysis of spontaneous response in skin conductance, caused by pain or similar activities in the autonomous nervous system of the individual.

U.S. Pat. No. 4,697,599 discloses an example of a previously known apparatus for detection of pain, based on measurement of the skin's conductance. The apparatus exhibits a measurement on a display, in addition to which it emits an audible signal which has a pulse frequency which varies in accordance with the measured conductance. The apparatus only supplies information on the immediate value of the conductance, and does not analyse the measurements with regard to the frequency and amplitude of spontaneous fluctuations. The apparatus moreover uses a direct current-based resistance measurement, which can lead to side effects from the skin's polarisation properties.

GB-A-2.291.971 describes an example of an apparatus for visual biofeedback therapy. The apparatus is based on the visualisation of an autonomous activity for the patient. This is achieved by a result of the autonomous activity being measured by a measuring device, which in this case may comprise a sensor for measuring the skin's conductance. The result of the measurement then influences an image which is displayed to the patient. A feedback loop is thereby created which can enable the patient to train himself to reproduce relaxation exercises which alter the measured value in the desired direction. There is no indication that the apparatus comprises equipment for analysing spontaneous fluctuations, including their amplitude and frequency, in the measured conductance signal. Nor is there any indication that the apparatus has an area of application within the field of real time monitoring of a patient's sympathetic nervous system, including pain monitoring, but it is intended to be applied in the treatment of complaints such as, e.g., irritable stomach/bowel syndrome.

WO 86/01317 describes a method and an apparatus for utilising electrodermal response as a control body for a computer. In this case the skin's resistance is measured by means of a so-called paddle input body, equipped with electrodes, for a computer. In the method and the apparatus a certain amount of consideration is given to the dynamic of the resistance signal, not only the signal's immediate value, but also the signal change from one point of time to the next, being used in the calculation of a control signal. However, the publication gives no analysis of the amplitude and frequency of spontaneous signal fluctuations for monitoring purposes, and for detection of pain in particular. In this publication too resistance measurement based on direct current is employed, which may result in the skin's polarisation properties influencing the measurements.

Related solutions can also be found in the part of the technology which deals with lie detectors. Some lie detectors employ skin conductance as the basis of their analysis. However, such equipment does not make use of secondary characteristics in the skin conductance signal such as the frequency and amplitude of spontaneous fluctuations for real time monitoring of the activity in the sympathetic nervous system, and for detection of pain in particular.

Thus an object of the present invention is to provide an apparatus for monitoring the autonomous nervous system in an individual, especially for detecting pain, which is not encumbered by the disadvantages which are mentioned above.

According to the invention this is achieved by an apparatus as mentioned above, characterized in that it comprises the features which are indicated by the characterising part of the following independent claim 1.

It is a further object of the present invention to provide a method for controlling a warning signal in an apparatus for monitoring the autonomous nervous system in an individual, especially for detecting pain, and which is not encumbered by the said disadvantages.

According to the invention this is achieved by a method as mentioned above, characterized in that it comprises the features which are indicated by the characterising part of the following independent claim 6.

Finally, it is an object of the present invention to provide a method for monitoring the autonomous nervous system in an individual, especially for detecting pain, and which is not encumbered by the said disadvantages.

According to the invention this is achieved by a method as mentioned above, characterized in that it comprises the features which are indicated by the characterising part of the following independent claim 10.

Further advantages and characteristics are indicated in the dependent claims.

Figure 2:
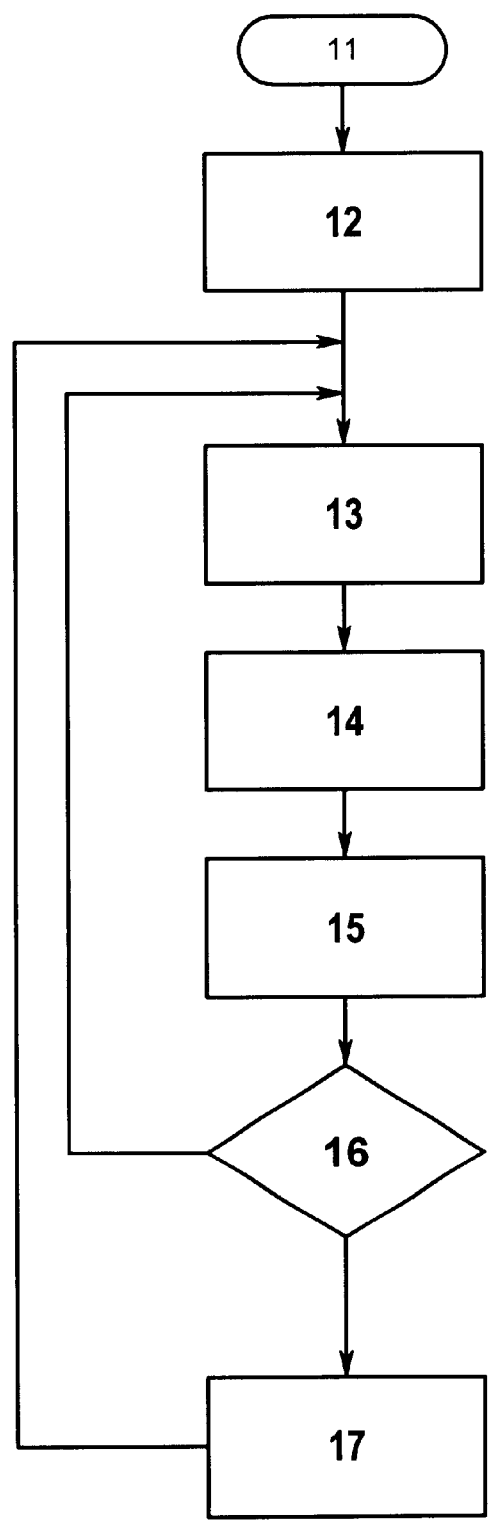

The apparatus and methods according to the invention will now be described in more detail with reference to the attached drawings, in which FIG. 1 illustrates a block diagram for an apparatus according to the invention, and FIG. 2 illustrates a flow chart for a method according to the invention.

FIG. 1 illustrates a block diagram for a preferred embodiment of an apparatus according to the invention. The apparatus is particularly arranged for real time detection of pain reaction in an individual, for example a patient. On an area 2 of the skin on a body part 1 of an individual, sensor means 3 are placed for measuring the skin's conductance. The body part 1 is preferably a hand or a foot, and the area 2 of the skin on the body part 1 is preferably the palmar side of the hand (in the palm of the hand) or the plantar side of the foot (under the sole of the foot). The sensor means 3 advantageously comprise contact electrodes where at least two electrodes are placed on the skin area 2. In a preferred embodiment the sensor means 3 consist of three electrodes: a measuring electrode, a counter electrode and a reference voltage electrode which ensures a constant application of voltage over the stratum corneum (the surface layer of the skin) under the measuring electrode. The measuring electrode and the counter electrode are preferably placed on the skin area 2. The reference voltage electrode may also be placed on the skin area 2, but it is preferably placed in a nearby location, suitable for the measuring arrangement concerned.

In a preferred embodiment an alternating current is used for measuring the skin's conductance. The alternating current advantageously has a frequency in the range up to 1000 Hz, corresponding to the area where the skin's conductance is approximately linear. A frequency should be selected which ensures that the measuring signal is influenced to the least possible extent by interference from, e.g., the mains frequency. In a preferred embodiment the frequency is 88 Hz.

In the case of alternating current the conductance is identical to the real part of the complex admittance, and therefore not necessarily identical with the inverse value of the resistance. An advantage of using alternating current instead of direct current in conductance measurement is that by this means one avoids the invidious effect on the measurements of the skin's electrical polarising properties.

The resulting current through the measuring electrode is conveyed to a measurement converter 4. This comprises a current to voltage converter which in a preferred embodiment is a transresistance amplifier, but in its simplest form may be a resistance which converts the current from the measuring electrode to a voltage. The measurement converter further comprises a decomposition circuit, preferably in the form of a synchronous rectifier which decomposes the complex admittance in a real part (the conductance) and an imaginary part (the susceptance). However, it is sufficient if the decomposition circuit only comprises means for deriving the conductance.

The measurement converter 4 may also comprise amplifier and filter circuits. In the preferred embodiment the measurement converter contains a low-pass filter. The object of the filter circuits may be partly to damp high-frequency noise, and partly to serve as anti-aliasing filters for preventing higher frequency components from being received by subsequent circuits for time discretization. By means of the choice of components and design details, moreover, the measurement converter is designed with a view to obtaining high sensitivity and a low noise level.

The control unit 5 comprises means for time discretization of the signal from the measurement converter. The time discretization takes place at a sampling rate which may advantageously be in the order of 20 to 200 samplings per second. The control unit further comprises an analog-digital converter, which converts measurement data to digital form. The choice of circuits for time discretization and analog-digital convertion represent technical decisions for a person skilled in the art.

The control unit may advantageously comprise additional analog and possibly also digital inputs, in addition to the input from the measurement converter. In this case the control unit can either be equipped with a plurality of analog-digital converters, or it can employ various multiplexing techniques well-known to those skilled in the art in order to increase the number of inputs. These additional analog inputs may, for example, be arranged for additional electrodermal measurements, or for other physiological measurements which may advantageously be performed simultaneously or parallel with the electrodermal measurement, such as temperature, pulse, ECG, respiratory and frequency measurements or oxygen saturation measurements in the blood.

The control unit 5 also comprises processing means for processing the digitised measurement data, storage means in the form of at least one store for storing data and programs, and adaptation circuits for giving at least one warning signal 7 to a signal unit 6, preferably also a signal for displaying information on display means 8. The control unit 5 may also advantageously comprise a communication port for digital communication with an external unit, such as a computer. Such communication is well-suited for loading or altering the program which is kept stored in the storage means in the control unit, or for adding or altering other data which are kept stored in the storage means in the control unit, such as threshold values, which will be discussed later. Such communication is also well-suited for read-out of data from the storage means in the apparatus, thus enabling them to be transferred to an external computer for further, subsequent analysis or storage. A communication port in the control unit will be advantageously designed in accordance with requirements for equipment safety for patients, as described in more detail below.

In a preferred embodiment the storage means comprise a read-only storage in the form of programmable ROM circuits, containing at least a program code and permanent data, and a read and write storage in the form of RAM circuits, for storage of measurement data and other provisional data.

The control unit 5 also comprises an oscillator which delivers a clock signal for controlling the processing means. The processing means also contain timing means in order to provide an expression of the current time, for use in the analysis of the electrodermal measurements. Such timing means are well-known to those skilled in the art, and are often included in microcontrollers or processor systems which are suitable for use with the invention.

The control unit 5 may be realised as a microprocessor-based unit with connected input, output, memory and other peripheral circuits, or it may be realised as a microcontroller unit where some or all of the connected circuits are integrated. The means for time discretization and/or analog-digital conversion may also be integrated in such a unit. The choice of a suitable form of control unit involves evaluations which are standard for a person skilled in the art.

An alternative solution is to realise the control unit as a digital signal processor (DSP).

The control unit 5 is arranged to read in time-discrete and quantized measurements for the skin conductance from the measurement converter 4, preferably by means of a program code which is stored in the storage means and which is executed by the processing means. It is further arranged to enable measurements to be stored in the storage means, preferably in a read and write store. The control unit is further arranged to analyse the measurements in real time, i.e. simultaneously or parallel with the performance of the measurements. In this context, simultaneously or parallel should be understood to mean simultaneously or parallel for practical purposes, viewed in connection with the time constants which are in the nature of the measurements. This means that input, storage and analysis can be undertaken in separate time intervals, but in this case these time intervals, and the time between them, are so short that the individual actions appear to occur concurrently.

The control unit is further arranged to identify the fluctuations in the time-discrete, quantized measuring signal, preferably by means of a program code which is stored in the storage means and which is executed by the processing means, and to derive analysis data expressing the frequency and the amplitude of the fluctuations in the measuring signal.

In the control unit's storage means threshold data are stored representing limiting values for the analysis data which are derived from the measurements, corresponding to the conditions which will result in the analysis of the measurements activating the warning signal 7 and thereby a signal device 6. The threshold data therefore correspond to a presumed limit for pain or similar activity in the individual's sympathetic nervous system.

In the simplest form the threshold data can be universal, since they apply to every individual on whom the apparatus or the method is used. The threshold data preferably constitute values characterising an individual group to which the patient belongs. This grouping may depend on individual factors such as age, sex and/or possible diagnosis.

Alternatively, the threshold data may constitute quite specific values, uniquely linked to the individual.

The processing means are arranged to compare the threshold data with the derived analysis data expressing the frequency and amplitude of the fluctuations in the measuring signal. The result of this comparison expresses whether or not the warning signal 7 will activate the signal device 6.

The warning signal 7 is preferably a digital signal, which indicates that the real time analysis of the skin conductance measurement has resulted in a threshold for presumed pain reaction being exceeded. The warning signal 7 activates a signal or warning device 6, which may be any suitable device for visual or audible warning. Alternatively, the warning signal may be transferred to or activate an external communication or monitoring system, for example an external system for remote monitoring of patients.

In a special application of the invention the warning signal 7 or another signal derived from the processing means in the analysis of the skin conductance measurements may be used to control an automatic administration of a medication to the individual, particularly an analgesic medication or a sleep-inducing medication. The signal may be used, for example, to control a pump for intravenous supply of morphine. In this case the invention will form part of a feedback loop for control of the activity in the individual's autonomous nervous system.

In a preferred embodiment the display means 8 consist of a screen for graphic visualisation of the conductance signal, and a digital display for displaying the frequency and amplitude of the measured signal fluctuations. The display units are preferably of a type whose power consumption is low, such as an LCD screen and LCD display. The display means may be separate or integrated in one and the same unit.

The apparatus further comprises a power supply unit 9 for supplying operating voltage and current to the various parts of the apparatus. The power supply may be a battery or a mains supply of a known type.

The apparatus may advantageously be adapted to suit the requirements regarding hospital equipment which ensures patient safety. Such safety requirements are relatively easy to fulfil if the apparatus is battery-operated. If, on the other hand, the apparatus is mains operated, special requirements must be met by the power supply unit, or requirements are made regarding a galvanic partition between parts of the apparatus (for example, battery operated) which are safe for the patient and parts of the apparatus which are unsafe for the patient. If the apparatus has to be connected to external equipment which is mains operated and unsafe for the patient, the connection between the apparatus which is safe for the patient and the unsafe external equipment requires to be galvanically separated. Galvanic separation of this kind can advantageously be achieved by means of an optical partition. Safety requirements for equipment close to the patient and solutions for fulfilling such requirements in an apparatus like that in the present invention are well-known to those skilled in the art.

FIG. 2 illustrates a flow chart for a method for controlling a warning signal in an apparatus for monitoring the autonomous nervous system of an individual, and especially for detecting pain.

The method starts at reference 11.

Firstly, initial conditions 12 for the method are established. A vital step here is to establish threshold data, as mentioned above. These threshold data constitute limiting values for the analysis data which are derived from the measurements, corresponding to the conditions which will result in the real time analysis of the measurements activating the warning signal 7 and thereby a signal device 6. Thus the threshold data correspond to a presumed limit for pain or similar activity in the individual's sympathetic nervous system.

A repeated monitoring process is then carried out, comprising the following actions:

The conductance of at least one area of the individual's skin is measured 13. The measurement may be continuous or time-discrete. In the preferred embodiment the actual measurements are made with electrodes 3 and a measurement converter 4 continuously in time, and the measuring signal is made time-discrete in the subsequent control unit 5.

The measurements or data associated with the measurements at discrete points of time are stored 14 in the storage means in the control unit.

An analysis 15 is made of current and previously recorded measurements. Analysis data is preferably derived expressing the frequency and amplitude of the fluctuations in the measuring signal. In a preferred embodiment these data are provided by considering the measuring signal's local maximum values and minimum values in a time window consisting of an interval containing recently elapsed points of time. The existence of a minimum and maximum value is established if the change in the signal value is essentially zero over a limited, recently elapsed period in the interval.

In the interval analysis data are formed for the amplitude by calculating the mean value of the differences from a minimum value to the following maximum value. Analysis data for the frequency are preferably formed by counting the number of maximum values contained in the interval.

Alternatively, the measuring signal or a section of the measuring signal's history can be decomposed (for example by digital filtering) into a slowly varying part, which constitutes the so-called basal line for the measurements, and a more rapidly varying part, which constitutes the fluctuations. Figures are then derived for the frequency and amplitude of the fluctuation component of the measuring signal.

The analysis of the measuring signal may involve more comprehensive methods, including methods which transform from the time plane to the frequency plane, for example real time Fourier transformation, where such analysis also derives analysis data expressing the frequency and amplitude of the signal fluctuations.

The figures which are derived by the analysis are compared 16 with the stored threshold values. In the event of a negative comparison, which means that the limit for pain or other activity in the individual's autonomous nervous system has not been reached, the monitoring cycle is repeated. In the event of a positive comparison, which indicates that a limit for pain or other autonomous nervous system activity has been reached, the warning signal 7 is activated 17.

In the analysis it may be necessary to establish special criteria for when a maximum value should be considered valid. In their simplest form such criteria may be based on the fact that the signal has to exceed an absolute limit in order to be able to be considered a maximum value. In addition, it is an advantage to base the criteria on the fact that the signal has formed a peak which has lasted a certain time, thus preventing extremely brief noise pulses from being considered as maximum values. The criteria may also be based on the fact that the increase in the signal value as a function of time must remain below a certain limit if the maximum value is to be considered valid. The object is thereby achieved that artefacts which can occur in error situations such as, e.g., electrodes working loose from the skin, are not considered as valid maximum values.

The above-mentioned criteria may be linked to the individual patient or to a group to which the patient belongs. This grouping is preferably based on age, but may also include individual factors such as sex and/or possible diagnosis.

A set of specially recommended criteria for validity of a maximum value is as follows:

Absolute minimum limit for measured conductance: for adults 0.02 $\mu$S, for children 0–02 $\mu$S, for premature babies 0.015 $\mu$S Minimum duration of a top: for adults 0.0 s, for children 0.0 s Maximum increase just prior to the maximum value: for adults 2 $\mu$S/s, for children 2 $\mu$S/s If necessary or desirable corresponding criteria may also be established for the validity of minimum values.

The above description with drawings present a specific embodiment of the invention, with the addition of some alternatives. For a person skilled in the art, however, it will be obvious that other, alternative embodiments exist which are within the scope of the present invention, as indicated in the following patent claims.

What is claimed is:

1. An apparatus for monitoring the autonomous nervous system in an individual for determining pain, comprising:
   measuring equipment for continuous or time-discrete measurement of the conductance of at least one area of the individual's skin,
   storage means for storing data associated with measurements of the conductance at discrete points of time,
   storage means for storing threshold data,
   processing means for analysing current and previous measurements of the conductance, and for comparing analysis data produced by this analysis with said threshold data, and
   signal means for indicating or warning when the comparison between said analysis data and said threshold data fulfils predetermined conditions indicative of pain.

2. An apparatus according to claim 1, wherein the measuring equipment comprises a sensor comprising at least two electrodes, wherein said at least two electrodes are arranged to be placed on the area of the individual's skin where the conductance is to be measured.

3. An apparatus according to claim 2, wherein the said processing means are also arranged to control a device for administering medication to the individual.

4. An apparatus according to claim 1, wherein the measuring equipment comprises a measurement converter which provides conductance measurements by allowing at least a part of the area of the individual's skin to conduct an alternating current, by measuring the skin area's complex admittance, and by deriving the conductance component from the measured admittance.

5. An apparatus according to claim 4, wherein the said processing means are also arranged to control a device for administering medication to the individual.

6. An apparatus according to claim 1, wherein the processing means comprises means for deriving secondary characteristics of the measured and stored conductance signal in a time interval, wherein the secondary characteristics comprise the frequency and amplitude of fluctuations in the signal.

7. An apparatus according to claim 6, wherein the said processing means are also arranged to control a device for administering medication to the individual.

8. An apparatus according to claim 1, further comprising a means for displaying characteristics of the measured conductance signal, which characteristics include waveform of the signal, frequency of fluctuations in the signal and/or amplitude of fluctuations in the signal.

9. An apparatus according to claim 8, wherein the said processing means are also arranged to control a device for administering medication to the individual.

10. An apparatus according to claim 1, wherein the said processing means are also arranged to control a device for administering medication to the individual.

11. A method for controlling a warning signal in an apparatus for monitoring the autonomous nervous system of an individual for determining pain, the method comprising steps of:
   initially establishing and retaining stored threshold data,
   thereafter implementing a monitoring process which comprises
      continuously or time-discretely measuring the conductance of at least one area of an individual's ski,
      storing measurements of the conductance,
      deriving analysis data for current and previous measurements of the conductance,
      comparing said analysis data with said threshold data,
      activating the warning signal if the comparison between said analysis data and said threshold data fulfils predetermined conditions indicative of pain.

12. A method according to claim 11, the measuring step further comprises:
   allowing at least a part of the area of the individual's skin to conduct an alternating current,
   measuring the complex admittance of this part of the skin; and
   deriving the conductance component from the measured admittance.

13. A method according to claim 12, wherein the derivation of analysis data from current and previous measurements comprises recording local maximum and minimum values for the signal in a time interval, and letting the analysis data represent the mean value of the differences from a maximum value to the following maximum value over the time interval, and the number of maximum values contained in the time interval.
   controlling a device for administering medication to the individual on the basis of derived analysis data.

14. A method according to claim 12, further comprising:
   controlling a device for administering medication to the individual on the basis of derived analysis data.

15. A method according to claim 11, wherein the deriving step further comprises:
   determining secondary characteristics of the signal which is composed of the current and previous measurements, which characteristics include the frequency and amplitude of fluctuations in the signal.

16. A method according to claim 15, wherein the derivation of analysis data from current and previous measurements comprises recording local maximum and minimum values for the signal in a time interval, and letting the analysis data represent the mean value of the differences from a minimum value to the following maximum value over the time interval, and the number of maximum values contained in the time interval.

17. A new method according to claim 15, further comprising:
   controlling a device for administering medication to the individual on the basis of derived analysis data.

18. A method according to claim 11, wherein the derivation of analysis data from current and previous measurements comprises recording local maximum and minimum values for the signal in a time interval, and letting the analysis data represent the mean value of the differences from a minimum value to the following maximum value over the time interval, and the number of maximum values contained in the time interval.

19. A method according to claim 18, further comprising:
    controlling a device for administering medication to the individual on the basis of derived analysis data.

20. A method according to claim 11, further comprising:
    controlling a device for administering medication to the individual on the basis of derived analysis data.

21. A method for monitoring the autonomous nervous system of an individual for determining pain, the method comprising steps of:
    initially establishing and retaining stored threshold data, thereafter implementing a monitoring process which comprises
        continuously or time-discretely measuring the conductance of at least one area of an individual's skin,
        storing measurements of the conductance,
        deriving analysis data for current and previous measurements of the conductance,
        comparing said analysis data with said threshold data,
        establishing increased activity in the autonomous nervous system in the individual, especially increased pain reaction, if the comparison between said analysis data and said threshold data fulfils predetermined conditions indicative of pain.

* * * * *